United States Patent [19]

Koppe et al.

[11] 3,954,872
[45] May 4, 1976

[54] 1-(2',6'-DIMETHYL-PHENOXY)-2-AMINO-ALKANES AND SALTS THEREOF

[75] Inventors: Herbert Köppe; Karl Zeile; Werner Kummer; Helmut Stähle; Peter Danneberg, all of Ingelheim am Rhein, Germany

[73] Assignee: Boehringer Ingelheim GmbH, Ingelheim am Rhein, Germany

[22] Filed: Oct. 1, 1974

[21] Appl. No.: 511,063

Related U.S. Application Data

[63] Continuation-in-part of Ser. No. 86,983, Nov. 4, 1970, abandoned, which is a continuation-in-part of Ser. No. 871,619, Nov. 14, 1969, abandoned, which is a continuation of Ser. No. 667,665, Sept. 14, 1967, abandoned.

[30] Foreign Application Priority Data

Sept. 16, 1966  Germany................................. 88950
Aug. 17, 1967  Germany................................. 94024

[52] U.S. Cl.............................. 260/570.7; 260/254;
   260/501.17; 260/501.19; 260/566 A;
   424/253; 424/316; 424/330
[51] Int. Cl.²......................................... C07C 93/06
[58] Field of Search.......... 260/254, 501.17, 501.19,
   260/570.7

[56] References Cited
UNITED STATES PATENTS 3,235,597  2/1966  Mills et al......................... 260/570.7

3,515,741  6/1970  Thoma et al..................... 260/570.7

OTHER PUBLICATIONS

Durant et al., "Journal Med. Chem.", Vol. 9, No. 1, pp. 22–27 (1966).

*Primary Examiner*—Robert V. Hines
*Attorney, Agent, or Firm*—Hammond & Littell

[57] ABSTRACT

Compounds of the formula

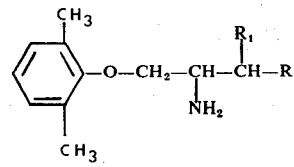

wherein
  R is hydrogen or alkyl of 1 to 3 carbon atoms, and
  $R_1$ is hydrogen or methyl,
and non-toxic, pharmacologically acceptable acid addition salts thereof; the compounds as well as their salts are useful as anticonvulsives and antiarrhythmics in warmblooded animals.

4 Claims, No Drawings

1-(2',6'-DIMETHYL-PHENOXY)-2-AMINO-ALKANES AND SALTS THEREOF

This is a continuation-in-part of copending application Ser. No. 86,983, filed Nov. 4, 1970, which in turn is a continuation-in-part of copending application Ser. No. 871,619, filed Nov. 14, 1969, now abandoned; which in turn is a continuation of application Ser. No. 667,665, filed Sept. 14, 1967, now abandoned.

This invention relates to novel 1-(2',6'-dimethyl-phenoxy)-2-amino-alkanes and acid addition salts thereof, as well as to various methods of preparing these compounds.

More particularly, the instant invention relates to racemic mixtures or optically active antipodes of 1-(2',6'-dimethyl-phenoxy)-2-amino-alkanes of the formula

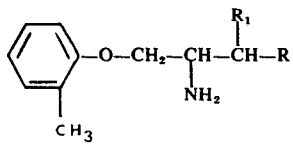

(I)

wherein
R is hydrogen or alkyl of 1 to 3 carbon atoms, and
$R_1$ is hydrogen or methyl,
and non-toxic, pharmacologically acceptable acid addition salts thereof.

The compounds according to the present invention may be prepared by a number of methods involving well known chemical principles, among which the following have proved to be particularly convenient and efficient:

Method A

By splitting off one or two monovalent or one bivalent protective group from a compound of the formula

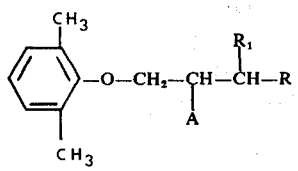

(II)

wherein R and $R_1$ have the same meanings as in formula I, and A is a secondary or tertiary amino group having one or two readily removable protective substituents, such as benzyl, phthalyl, toluenesulfonyl or formyl, attached thereto. The removal of the protective group may be achieved by conventional methods, such as by catalytic hydrogenation.

A starting compound of the formula II may be obtained by reacting a corresponding 1-(2',6'-dimethyl-phenoxy)-2-halo-alkane with a suitable primary or secondary amine, or by reacting a corresponding 1-(2',6'-dimethyl-phenoxy) -2-oxo-alkane with a suitable primary amine under reducing conditions.

Method B

By reacting a compound of the formula

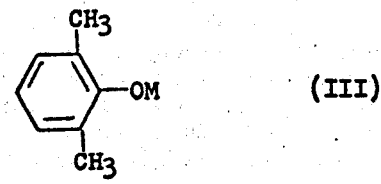

(III)

wherein M is hydrogen or a metal cation, with a compound of the formula

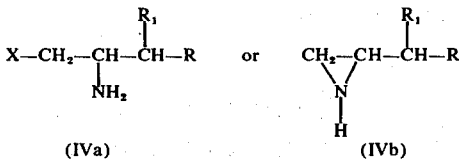

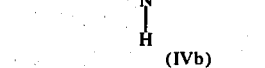

wherein R and $R_1$ have the same meanings as in formula I, and X is the radical of a reactive ester, such as a halogen atom, particularly chlorine or bromine.

A compound of the formula IVa or IVb may be prepared by conventional methods, such as those described in British Patent No. 765,849 or in Houben-Weyl, 4th Edition (1958), Vol. XI/2, pages 228–230.

Method C

By reducing a compound of the formula

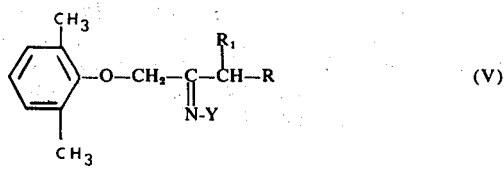

(V)

wherein R and $R_1$ have the same meanings as in formula I, and Y is hydrogen, hydroxyl or amino, with catalytically activated hydrogen or a complex metal hydride.

A starting compound of the formula V may be obtained by reacting a corresponding 1-(2',6'-dimethyl-phenoxy)-2-oxo-alkane with ammonia, hydroxylamine or hydrazine. A 1-(2',6'-dimethyl-phenoxy)-2-oxo-alkane, in turn, may be obtained by reacting a phenolate of the formula III with a 1-halo-2-oxo-alkane of corresponding carbon chain length.

The compounds of the formula I above contain an asymmetrically substituted carbon atom bonded to the free amino group and, therefore, occur in the form of racemic mixtures as well as optically active antipodes. The racemic mixtures may be divided into their optically active antipode components by conventional methods, for instance, by salt formation with optically active acids such as D-3-bromocamphor-8-sulfonic acid or dibenzoyl-D-tartaric acid. Another method of obtaining an optical antipode is by starting with the corresponding optically active antipode of compound II in method A.

The compounds of the formula I are organic bases and therefore form acid addition salts with inorganic or organic acids. Such acid addition salts may be obtained in customary fashion, such as by dissolving the free base in a suitable solvent and acidifying the solution with the desired inorganic or organic acid. Examples of non-toxic, pharmacologically acceptable acid addition salts are those formed with hydrochloric acid, hydrobromic acid, sulfuric acid, maleic acid, acetic acid, oxalic acid, lactic acid, tartaric acid, succinic acid, methanesulfonic acid, 8-chlorotheophyllinc or the like.

The following examples further illustrate the present invention and will enable others skilled in the art to understand it more completely. It should be understood, however, that the invention is not limited to the particular examples given below.

EXAMPLE 1

Preparation of 1-(2',6'-dimethyl-phenoxy)-2-amino-propane and its hydrochloride by method C 245 gm of 1-(2',6'-dimethyl-phenoxy)-propanone-(2)-oxime were dissolved in 1300 cc of methanol, and the solution was hydrogenated at 5 atmospheres gauge and 60°C. in the presence of Raney nickel. After the calculated amount of hydrogen had been absorbed, the catalyst was filtered off, the methanol was distilled out of the filtrate, and the residue, raw 1-(2',6'-dimethyl-phenoxy)-2-amino-propane, was dissolved in ethanol. The resulting solution was acidified with ethereal hydrochloric acid, the acidic solution was allowed to cool, and the precipitate formed thereby was collected by vacuum filtration. The filter cake was dissolved in ethanol and recrystallized therefrom by addition of ether. 140.5 gm (51.5% of theory) of a substance having a melting point of 203–205°C. were obtained, which was identified to be 1-(2',6'-dimethyl-phenoxy)-2-amino-propane hydrochloride of the formula

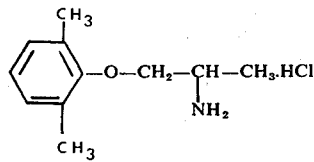

EXAMPLE 2

Preparation of 1-(2',6'-dimethyl-phenoxy)-2-amino-butane and its hydrochloride by method C 18.3 gm (0.095 mol) of 1-(2',6'-dimethyl-phenoxy)-butanone-(2) were refluxed with 14 gm (0.2 mol) of hydroxylamine hydrochloride in 100 cc of ethanol in the presence of 25 cc of water and 20 cc of pyridine, yielding 17.6 gm of raw 1-(2',6'-dimethyl-phenoxy)-butanone-(2)-oxime, which was dissolved in 50 cc of methanol, and the solution was hydrogenated at 60°C. and 5 atmospheres gauge in the presence of Raney nickel. After the calculated amount of hydrogen had been absorbed, the catalyst was filtered off, the metha-nol was distilled out of the filtrate, the residue digested with water, the aqueous mixture was acidified with hydrochloric acid, and the neutral component was extracted with ether. The acid aqueous phase was made alkaline with ammonia, the oily precipitate formed thereby was taken up in ether, the ethereal solution was dried over magnesium sulfate, and the ether was distilled off. The residue, 12.6 gm of 1-(2',6'-dimethyl-phenoxy)-2-amino-butane, was dissolved in ethanol, the resulting solution was acidified with ethereal hydrochloric acid, and the crystalline precipitate formed thereby was collected and recrystallized twice from ethanol/ether. 8.2 gm of a substance having a melting point of 210–211°C. was obtained, which was identified to be 1-(2',6'-dimethyl-phenoxy)-2-amino-butane hydrochloride of the formula

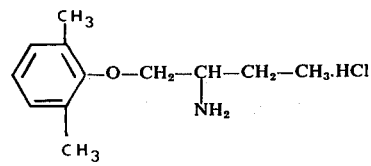

EXAMPLE 3

Using a procedure analogous to that described in Example 1, 1-(2',6'-dimethyl-phenoxy)-2-amino-pentane and its hydrochloride, m.p. 230–231°C., were prepared from 1-(2',6'-dimethyl-phenoxy)-pentanone-(2).

EXAMPLE 4

Using a procedure analogous to that described in Example 2, 1-(2',6'-dimethyl-phenoxy)-2-amino-3-methyl-butane and its hydrochloride, m.p. 170°C., were prepared from 1-(2',6'-dimethyl-phenoxy)-3-methyl-butanone-(2).

EXAMPLE 5

Preparation of 1-(2',6'-dimethyl-phenoxy)-2-amino-hexane and its hydrochloride by method C 13 gm (0.05 mol) of 1-(2',6'-dimethyl-phenoxy)-hexanone-(2)-oxime, obtained from 2',6'-dimethyl-phenoxy-methyl-n-butyl ketone and hydroxylamine hydrochloride, were dissolved in methanol, and the solution was hydrogenated in a shaker autoclave at 60°C. and 5 atmospheres gauge in the presence of Raney nickel as a catalyst. After the theoretical amount of hydrogen had been absorbed, the catalyst was removed by vacuum filtration, and the methanol was distilled out of the filtrate. The residue was dissolved in ether, and the filtrate, an ethereal solution of the free base 1-(2',6'-dimethyl-phenoxy)-2-amino-hexane, was acidified with ethereal hydrochloric acid to acid reaction of Congo Red. The white crystalline precipitate formed thereby was collected by vacuum filtration, and the filter cake was washed with ether and dried. 4.0 gm (31.1% of theory) of analytically pure and thin-layer chromatographically uniform 1-(2',6'-dimethyl-phenoxy)-2-amino-hexane hydrochloride, m.p. 209–211°C., of the formula

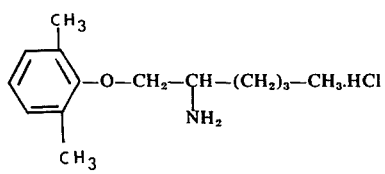

were obtained.

EXAMPLE 6

Preparation of
1-(2',6'-dimethyl-phenoxy)-2-amino-3-methyl-butane and its hydrochloride by method C 10.3 gm (0.05 mol) of 1-(2',6'-dimethyl-phenoxy)-3-methyl-butanone-(2) were dissolved in a mixture of 75 cc of ethanol and 8.5 gm of ammonia, and the resulting solution was allowed to stand for 16 hours at 20°C. Thereafter, while stirring, a solution of 3.7 gm of sodium borohydride in 100 cc of ethanol was added dropwise at 20°C., the mixture was stirred for 1 hour more and was then acidified with hydrochloric acid. The acid solution was evaporated in vacuo, the residue was admixed with water, and the aqueous phase was made alkaline with sodium hydroxide, the precipitate formed thereby was extracted with ether, the ethereal solution was dried over magnesium sulfate, the ether was distilled off, the residue, the free base 1-(2',6'-dimethyl-phenoxy)-2-amino-3-methyl-butane, was taken up in methanol, and the resulting solution was acidified with ethereal hydrochloric acid. The precipitate formed thereby was collected and recrystallized from a mixture of methanol and ether, yielding 6.2 gm of 1-(2',6'-dimethyl-phenoxy)-2-amino-3-methyl-butane hydrochloride, m.p. 170°C., of the formula

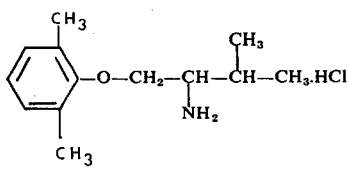

The compounds according to the present invention, that is, a racemic mixture of a compound of the formula I, an optically active antipode component thereof, or a non-toxic, pharmacologically acceptable acid addition salt of said racemic mixture or optical antipode, have useful pharmacodynamic properties. More particularly, they exhibit longlasting anticonvulsive and anti-arrhythmic activities without significant concurrent sedative side effects in warm-blooded animals, such as rats and mice.

Examples of specific compounds which are especially effective as anticonvulsive are 1-(2',6'-dimethyl-phenoxy)-2-amino-propane and its hydrochloride, and 1-(2',6'-dimethyl-phenoxy)-2-amino-pentane and its hydrochloride.

The anticonvulsive activity of the compounds of the present invention and of certain isomers and homologs described in the prior art was ascertained by the electroshock method of Tooman et al, J. Neurophysiol. 9, 231 (1946), and their toxicities were determined by the standard method for determination of the median lethal dose ($LD_{50}$).

The following table shows illustrative and representative results obtained from these tests, where A = 1-(2',6'-xylyloxy)-2-amino-propane, described in Example I above;
= N-methyl-2-(2',6'-xylyloxy)-ethylamine, disclosed by G. J. Durant et al, J. Med. Chem., Vol. 9, No. 1, 22 (1966);
C = 2-(2',6'-xylyloxy)-ethylamine, disclosed by G. J. Durant et al, supra; and
D = 3-(2',6'-xylyloxy)-propylamine, disclosed by Durant et al., supra.

| Compound | Anticonvulsive $ED_{50}$ mgm/kg mouse p.s. | $LD_{50}$ mgm/kg mouse p.o. | Therapeutic ratio $LD_{50}/ED_{50}$ |
|---|---|---|---|
| Invention: | | | |
| A | 23 | 430 | 18.7 |
| Prior art: | | | |
| B | 80 | 216 | 2.7 |
| C | 115 | 740 | 6.4 |
| D | 216 | 580 | 2.7 |

For pharmaceutical purposes, the compounds according to the present invention are administered to warm-blooded animals perorally or parenterally as active ingredients in customary dosage unit compositions, that is, compositions in dosage unit form consisting essentially of an inert pharmaceutical carrier and one dosage unit of the active ingredient, such as tablets, coated pills, capsules, wafers, solutions, suspensions, emulsions, syrups, suppositories or the like. One dosage unit of the compounds according to the present invention for peroral administration is from 0.016 to 5 mgm/kg body weight, preferably 0.5 to 3.3 mgm/kg body weight. For parenteral administration, one dosage unit of the compounds of the invention is from 0.0016 to 0.33 mgm/kg body weight.

A dosage unit composition pursuant to the instant invention may comprise one or more of the compounds of the invention as an active ingredient, provided the total unit dosage range set forth above is not exceeded. In addition, such a dosage unit composition may comprise a unit dose of one or more other pharmacodynamically active components, such as a tranquilizer of the benzodiazepine or phenothiazine type, or a spasmolytic of the scopolamine type.

The following examples illustrate a few dosage unit compositions comprising a compound according to the present invention as an active ingredient, and represent the best modes contemplated of putting the invention to practical use, The parts are parts by weight, unless otherwise specified.

EXAMPLE 7

Tablets

The tablet composition was compounded from the following ingredients:

| | | |
|---|---|---|
| 1-(2',6'-dimethyl-phenoxy)-2-amino-propane hydrochloride | 75.0 | parts |
| Lactose | 25.0 | " |
| Secondary calcium phosphate | 150.0 | " |
| Corn starch | 206.0 | " |
| Colloidal silicic acid | 12.0 | " |
| Stearic acid | 4.0 | " |
| Soluble starch | 8.0 | " |
| Total | 480.0 | parts |

Compounding procedure:

The phenoxypropane compound was intimately admixed with the lactose, the calcium phosphate, the corn starch and silicic acid, the resulting mixture was moistened with an aqueous solution of the soluble starch, and the moist mass was forced through a 1.5 mm - mesh screen. The moist granulate thus obtained was dried, admixed with the stearic acid, and the mixture was pressed into 480 mgm - tablets with the aid of a conventional tablet-making machine. Each tablet contained 75 mgm of the phenoxypropane compound and, when administered perorally to a warm-blooded animal of about 60 kg body weight in need of such treatment, produced very good anticonvulsive and antiarrhythmic effects.

EXAMPLE 8

Coated Pills

The pill core composition was compounded from the following ingredients:

| | | |
|---|---|---|
| 1-(2',6'-dimethyl-phenoxy)-2-amino-propane hydrochloride | 45 | parts |
| 1-(2',6'-methyl-phenoxy)-2-amino-pentane hydrochloride | 30 | '' |
| Secondary calcium phosphate | 120 | '' |
| Corn starch | 91 | '' |
| Colloidal silicic acid | 7 | '' |
| Magnesium stearate | 4 | '' |
| Polyvinylpyrrolidone | 3 | '' |
| Total | 300 | parts |

Compounding procedure:

The phenoxypropane compounds the calcium phosphate, the corn starch and the silicic acid were intimately admixed with each other, the mixture was moistened with an aqueous solution of the polyvinylpyrrolidone, and the moist mass was forced through a 1.5 mm - mesh screen. The moist granulate thus obtained was dried, admixed with the magnesium stearate, and the mixture was pressed into 300 mgm - pill cores with the aid of a conventional tablet-making machine. The pill cores were subsequently coated with a thin shell of a coating composition consisting essentially of sugar, titaniumdioxide, talcum, gum arabic and polyvinylpyrrolidone. Each coated pill contained 45 mgm of the dimethylphenoxyamino-propane compound and 30 mgm of the dimethylphenoxyamine-pentane compound and, when administered perorally to a warm-blooded animal of about 60 kg body weight in need of such treatment, produced very good antiarrhythmic and anticonvulsive effects.

EXAMPLE 9

Gelatin Capsules

The capsule filler composition was compounded from the following ingredients:

| | | |
|---|---|---|
| 1-(2',6'-dimethyl-phenoxy)-2-amino-propane maleate | 50 | parts |
| Lactose | 150 | '' |
| Total | 200 | parts |

Compounding procedure:

The phenoxypropane compound and the lactose were intimately admixed with each other, and 200 mgm - portions of the mixture were filled into individual gelatin capsules of suitable size. Each capsule contained 50 mgm of the phenoxypropane compound and, when administered perorally to a warm-blooded animal of about 60 kg body weight in need of such treatment, produced very good respiration-analeptic and anticonvulsive effects.

EXAMPLE 10

Tablets containing a compound of the invention and a tranquilizer

The tablet composition was compounded from the following ingredients:

| | | |
|---|---|---|
| 1-(2',6'-dimethyl-phenoxy)-2-amino-propane | 60 | parts |
| 5-Phenyl-7-chloro-1,3-dihydro-3-hydroxy-2H-1,4-benzodiazepin-2-one | 30 | '' |
| Calcium phosphate | 150 | '' |
| Corn starch | 206 | parts |
| Colloidal silicic acid | 12 | '' |
| Magnesium stearate | 4 | '' |
| Soluble starch | 8 | '' |
| Total | 470 | parts |

Compounding procedure:

The phenoxypropane compound, the benzodiazepinone compound, the calcium phosphate, the corn starch and the silicic acid were intimately admixed with each other, the mixture was moistened with an aqueous solution of the soluble starch, and the moist mass was forced through a 1.5 mm - mesh screen. The moist granulate thus obtained was dried, admixed with the magnesium stearate, and the mixture was pressed into 470mgm-tablets with the aid of a conventional tablet-making machine. Each tablet contained 60 mgm of the phenoxypropane compound and 30 mgm of the benzodiazepinone compound and, when administered perorally to a warm-blooded animal of about 60 kg body weight in need of such treatment, produced very good anticonvulsive, antiarrhythmic and tranquilizing effects.

EXAMPLE 11

Hypodermic Solution

The solution was compounded from the following ingredients:

| | | |
|---|---|---|
| 1-(2',6'-dimethyl-phenoxy)-2-amino-propane hydrochloride | 2.5 | parts |
| Sodium salt of EDTA | 0.2 | '' |
| Distilled water  q.s. ad | 1000.0 | '' by vol. |

Compounding procedure:

The phenoxypropane compound and the EDTA salt were dissolved in a sufficient amount of distilled water, the solution was filtered until free from suspended particles, the filtrate was filled into 2 cc - ampules, and the filled ampules were sterilized at 120°C. for 20 minutes and then sealed. Each ampule contained 5 mgm of the phenoxypropane compound, and when the contents of one ampule were administered by intramuscular injection to a warm-blooded animal of about 60 kg body weight in need of such treatment, they produced very good anticonvulsive and antiarrhythmic effects.

Although the above dosage unit composition examples illustrate only a few representative specific compounds of the present invention as active ingredients, it should be understood that any other compound embraced by formula I or a non-toxic acid addition salt thereof may be substituted for the particular phenoxyalkane compounds in Examples 7 through 11. Moreover, the amount of active ingredient in these examples may be varied to achieve the dosage unit ranges set forth above, and the amounts and nature of the inert pharmaceutical carrier components may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic or optically active compound of the formula

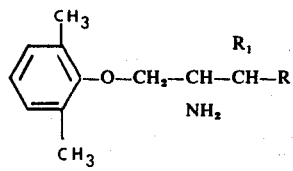

wherein
R is hydrogen or alkyl of 1 to 3 carbon atoms and
R$_1$ is hydrogen or methyl,
or a non-toxic, pharmacologically acceptable acid addition salt thereof.

2. A compound according to claim 1, which is racemic or optically active 1-(2',6'-dimethyl-phenoxy)-2-amino-propane or a non-toxic, pharmacologically acceptable acid addition salt thereof.

3. A compound according to claim 1, which is racemic or optically active 1-(2',6'-dimethyl-phenoxy)-2-amino-pentane or a non-toxic, pharmacologically acceptable acid addition salt thereof.

4. A compound according to claim 1, which is racemic or optically active 1-(2',6'-dimethyl-phenoxy)-2-amino-hexane or a non-toxic, pharmacologically acceptable acid addition salt thereof.

* * * * *

UNITED STATES PATENT OFFICE
CERTIFICATE OF CORRECTION

Patent No. 3,954,872　　　　　　　　Dated May 4, 1976

Inventor(s) Herbert Koppe et al.

It is certified that error appears in the above-identified patent and that said Letters Patent are hereby corrected as shown below:

Col. 1, Formula (I) 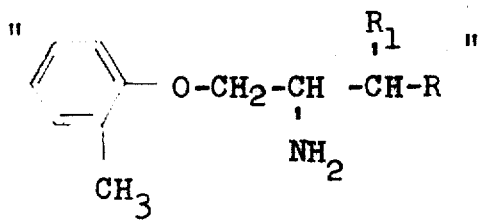 should be

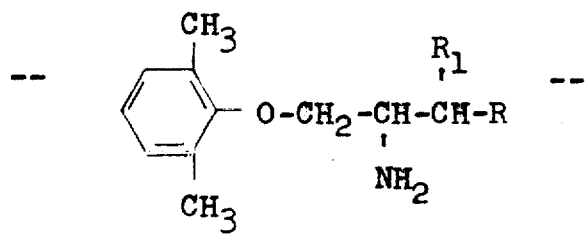

Col. 10, line 1
Formula 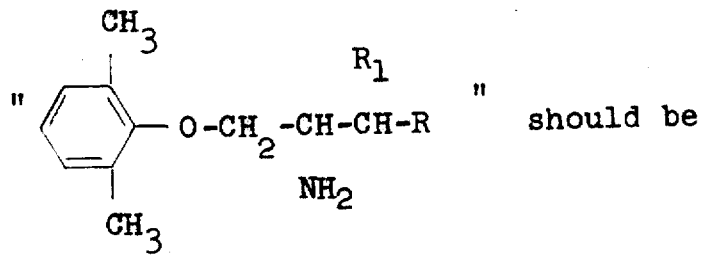 should be

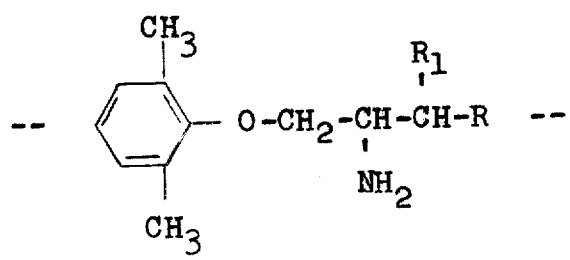

Signed and Sealed this

Twentieth Day of July 1976

[SEAL]

Attest:

RUTH C. MASON
*Attesting Officer*

C. MARSHALL DANN
*Commissioner of Patents and Trademarks*

UNITED STATES PATENT AND TRADEMARK OFFICE

CERTIFICATE EXTENDING PATENT TERM
UNDER 35 U.S.C. 156

Patent No.    : 3,954,872

Dated         : May 4, 1976

Inventor(s)   : Herbert Köppe, et al

Patent Owner  : Boehringer Ingelheim
                International GmbH

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this <u>Nineteenth</u> day of <u>December 1986</u>.

Donald J. Quigg

Assistant Secretary and Commissioner of Patents and Trademarks